US00PP10788P

United States Patent [19]

Lyrene

[11] Patent Number: Plant 10,788

[45] Date of Patent: Feb. 16, 1999

[54] BLUEBERRY PLANT NAMED 'SANTA FE'

[76] Inventor: Paul M. Lyrene, 2211 NW. 58th Ter., Gainesville, Fla. 32605

[21] Appl. No.: 943,104

[22] Filed: Jul. 18, 1997

[51] Int. Cl.[6] ..... A01H 5/00

[52] U.S. Cl. ..... Plt./33.1

[58] Field of Search ..... Plt./33.1

[56] References Cited

U.S. PATENT DOCUMENTS

| | | | |
|---|---|---|---|
| P.P. 7,974 | 9/1992 | Lyrene | Plt./33.1 |
| P.P. 8,082 | 1/1993 | Lyrene | Plt./33.1 |
| P.P. 8,083 | 1/1993 | Lyrene | Plt./33.1 |
| P.P. 9,834 | 3/1997 | Lyrene | Plt./33.1 |

OTHER PUBLICATIONS

Galletta, Gene J.; Blueberries and Cranberries; Advances in Fruit Breeding; 1975; pp. 154–185, 1975.

*Primary Examiner*—Howard J. Locker
*Assistant Examiner*—Kent L. Bell

[57] ABSTRACT

A new and distinct low-chill, tetraploid highbush blueberry (Vaccinium) variety of complex ancestry, based largely on *V. corymbosum* L with some genes from *V. darrowi* Camp. Its novelty consists of the following unique combination of features:

1. Produces a vigorous, upright, long-lived plant with little basal suckering.
2. Has high resistance to stem canker (*Botrosphaeria corticis*), stem blight (*Botryosphaeria dothedia,* and Phytophthora root rot.
3. Flowers and produces abundant new leaves in areas of north Florida where the mean temperature of the coldest month is 57° F. or lower.
4. Ripens its fruit 60 days after flowering in north-central Florida.
5. Ripens 80% of its fruit between April 20 and May 15 in north-central Florida.
6. Produces fruit that are large, firm, have a good picking scar, and a good flavor.
7. Can be propagated asexually by softwood cuttings.

2 Drawing Sheets

ORIGIN OF THE VARIETY

'Santa Fe' originated in 1975 by germination of open-pollinated seed from 'Avonblue', which was the female parent. The 'Avonblue' mother plant was growing in Earleton, Fla. in a selection block of the University of Florida blueberry breeding program. The male parent was an unidentified selection growing in this block. 'Avonblue' is an unpatented variety released from the University of Florida breeding program in 1977. A 3-plant clonal plot of 'Santa Fe' was observed for several years in Earleton, and based on its high vigor and berry quality, it was selected for further evaluation. A 15-plant clonal plot was established at the University of Florida Horticultural Unit in Gainesville, Fla. in 1987. Flowering date, ripening date, and fruit quality were evaluated annually in this plot through 1997. Other test plots of 'Santa Fe' were established at 5 other farms in north Florida in 1993. 'Santa Fe' was selected for release as a cultivar based on its high vigor, good plant survival, early ripening, and high-quality fruit.

ASEXUAL PROPAGATION OF THE VARIETY

The new and distinct variety has been propagated by softwood cuttings on numerous occasions. In every case, all the resulting plants have displayed the varietal characteristics without exception.

SUMMARY OF THE VARIETY

'Santa Fe' is vigorous and produces an upright plant with a low chill requirement. Although its chromosome number has not been determined cytologically, both its pedigree and its behavior indicate that it is tetraploid (2N=2X=48). 'Santa Fe' has been crossed on numerous occasions with other tetraploid cultivars, and the number of viable seedlings produced per pollinated flower has been high, whether it was used as the pollen or the seed parent. 'Santa Fe' breaks both leaf and flower bud without delay in the spring, but it normally flowers before it produces leaves in Gainesville. 'Santa Fe' plants have survived and maintained high vigor for 11 years at a site where most other highbush selections and cultivars have lost vigor or have died. The mean date when 50% of the flowers are open on 'Santa Fe' is March 1 in Gainesville. The date when the first 50% of the fruit are ripe averages May 3 in Gainesville. Berries are medium large (1.8 g per bush on plants with a medium crop load) and dark blue in color. The berry has a small, dry pedicel scar, good firmness, and a good post-harvest shelf life. The plant can be propagated by softwood cuttings, although it is harder to root than most other highbush cultivars.

DESCRIPTION OF THE VARIETY

Figure 1:
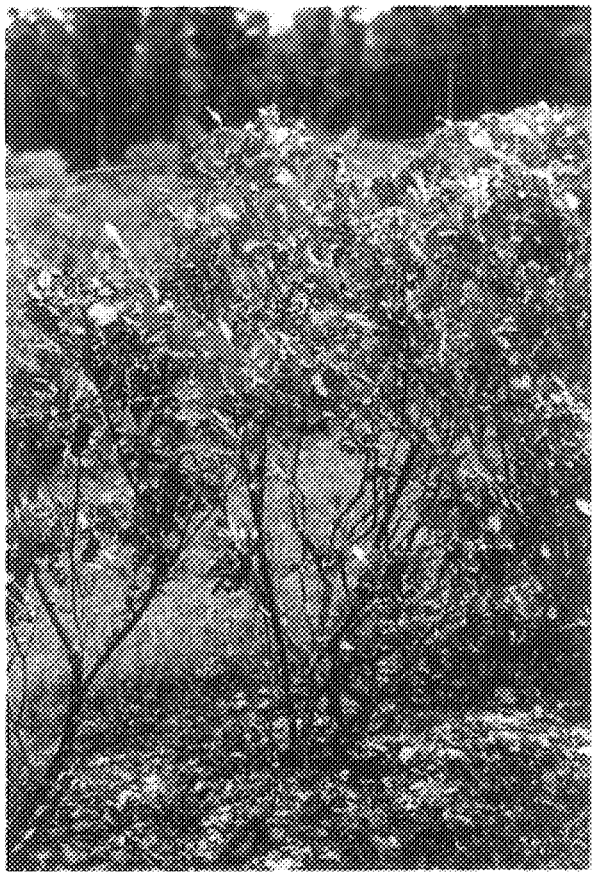
FIG. 1 illustrates several 10 year old specimens of the plant 'Santa Fe' in side elevation and shows the multiple trunk and branch scaffolding and also depicts the canopy and fruit clusters of the plant midway through the harvest period in early May in north-central Florida.
Figure 2:
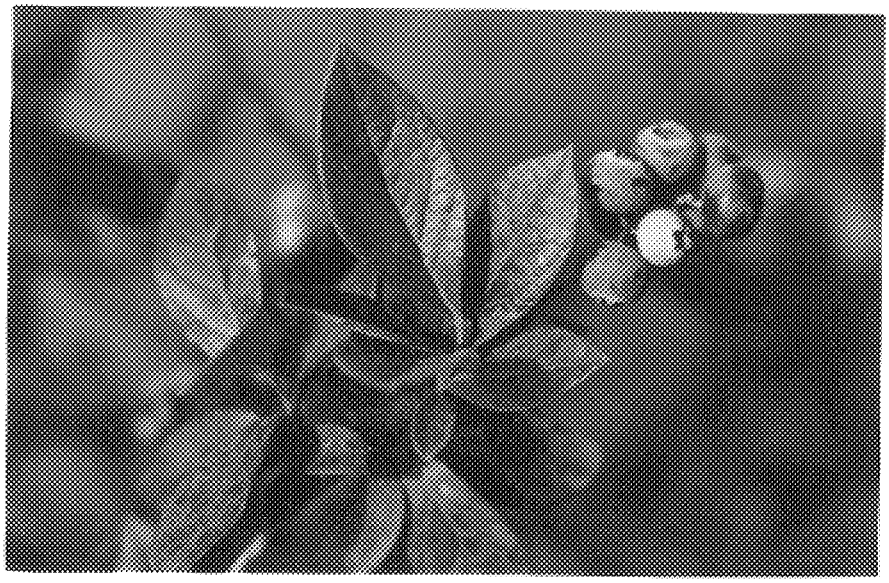
FIG. 2 shows, in larger scale, a fruit cluster of 'Santa Fe' as well as the top surface of foliage.
Figure 3:
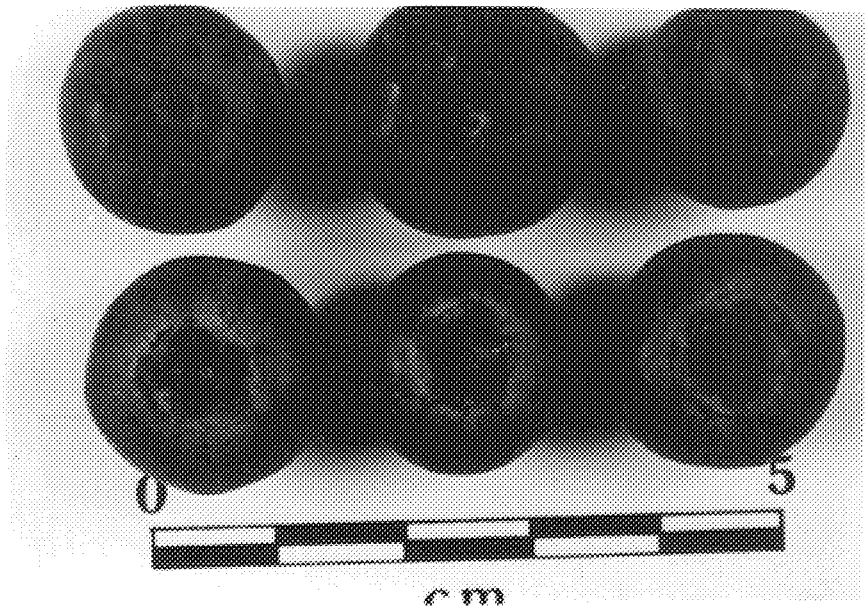
FIG. 3 depicts typical berries of 'Santa Fe' in even closer scale and shows the pedicel attachment scar as well as the corolla tube aperture of mature berries.

The following is a detailed botanical description of the new and distinct variety of blueberry, its flowers, fruit and foliage, based on observation of specimens grown in the field in Gainesville, Fla. Color descriptions, except those given in common terms, use terminology from "The Pantone Book of Color", by Leatrice Eiseman and Lawrence Herbert; Harry N. Abrams, Inc. Publishers, New York.

Bush:

*Size.*—Large. On good soil plants reach 2.2 m tall with a canopy diameter of 1.9 m after 10 years.

*Vigor.*—High.

*Growth habit.*—Upright; Forms a narrow crown.

*Productivity.*—High.

*Flower bud number.*—Moderately high.

*Cold hardiness.*—Except for the flowers and fruit, some of which have been killed in some years in Gainesville, Fla. by freezes in February and March, 'Santa Fe' has not suffered freeze damage in Gainesville. Dormant plants have withstood temperatures of 18° F. without damage. The cold tolerance appears typical of low-chill highbush blueberries.

*Chilling requirement.*—Based on the time of vegetative and floral bud break in Gainesville, Fla., 'Santa Fe' appears to have a chilling requirement of about 400 hours below 45° F.

*Productivity.*—Five year old plants of 'Santa Fe' yield about 6 pounds of fruit per plant per year when grown on favorable sites in north Florida and maintained with good cultural practices.

Trunk:

*Suckering tendency.*—Very limited basal sprouting. Ten-year-old, unpruned plants have only 2 to 8 major stems arising from a narrow basal crown.

*Texture.*—Bark on older trunks rough.

*Color.*—Mature trunk "feathery gray" (Pantone 15-1305).

Twigs:

*Color.*—Current-season twigs in full sun "shrimp" (Pantone 15-1523). Two-year-old twigs in full sun "dusty pink" (Pantone 14-1316).

*Internode length.*—For new shoots of moderate vigor, averages 14.8 mm.

Leaves:

*Size.*—Length of typical leaves 70 mm. Width of typical leaves 34 mm.

*Shape.*—Ovate, apically acute.

*Margin.*—Entire.

*Color of upper surface.*—"Chive" (Pantone 19-0323).

*Color of lower surface.*—"Tea" (Pantone 16-0213).

*Pubescence, upper surface.*—Numerous short, white hairs on midrib and major veins.

*Pubescence, lower surface.*—Inconspicuous or absent.

*Pubescence, leaf margins.*—Inconspicuous or absent.

Flowers:

*Length, bottom of ovary to corolla tip.*—11.4 mm.

*Diameter of corolla at widest point.*—7.7 mm.

*Corolla aperture diameter.*—4.3 mm.

*Color at anthesis.*—"Light lilac" (Pantone 12-2903).

*Pollen production.*—Copious.

*Pollen color.*—"Snow white" (Pantone 11-0602).

*Flower shape.*—Urceolate.

*Fragrance.*—Open flowers with slight honeysuckle fragrance.

*Flowering period.*—Early (February 10 to March 10, Gainesville).

*Inflorescence morphology.*—Pedicel length medium and peduncle internode length medium, leading to a moderately loose fruit cluster.

*Self compatibility.*—Partially self compatible but must be cross-pollinated with another tetraploid cultivar for full productivity.

*Reproductive organs.*—Androecium and Gynoecium typical for southern highbush blueberry styles as long as corolla tube, but not extending beyond the corolla tube.

Berry:

*Size.*—Medium to large, about 1.8 g per berry on plants with a medium-heavy crop.

*Height.*—13.6 mm.

*Width.*—17.3 mm.

*Diameter, calyx aperture, mature berry.*—7.3 mm.

*Color.*—"Lilac grey" (Pantone 14-3903).

*Pedicel scar.*—Small and dry.

*Firmness.*—Firm.

*Flavor.*—Sweet, slightly tart, somewhat aromatic.

*Texture.*—Good: small seeds, thin skins, few sclerids.

*Wax.*—Moderately persistent.

*Maturity date.*—Early season. Mid-harvest averages May 3 in Gainesville, Fla.

*Clusters.*—Normally 5 to 8 berries per peduncle.

I claim:

1. A new and distinct highbush blueberry plant, substantially as illustrated and described, characterized by its vigorous, upright, long-lived bush, low chilling requirement, and large, high-quality, early-ripening fruit, having the ability to be asexually propagated by softwood cuttings, the fruit being suitable for both fresh and processed markets.

* * * * *